(12) United States Patent  
McBride

(10) Patent No.: US 6,267,503 B1
(45) Date of Patent: Jul. 31, 2001

(54) MEDICAL IMAGING SYSTEMS

(75) Inventor: Margot McBride, Kilconquhhar (GB)

(73) Assignee: Glasgow Caledonian University Company Limited (GB)

( * ) Notice: Subject to any disclaimer, the term of this patent is extended or adjusted under 35 U.S.C. 154(b) by 0 days.

(21) Appl. No.: 09/297,969

(22) PCT Filed: Nov. 13, 1997

(86) PCT No.: PCT/GB97/03045

§ 371 Date: Jun. 21, 1999

§ 102(e) Date: Jun. 21, 1999

(87) PCT Pub. No.: WO98/20795

PCT Pub. Date: May 22, 1998

(30) Foreign Application Priority Data

Nov. 13, 1996 (GB) .................................................. 9623575

(51) Int. Cl.⁷ .................................................. A61B 6/08
(52) U.S. Cl. ....................................... 378/206; 250/462.1
(58) Field of Search ......................... 250/462.1; 356/375; 364/413.26; 378/69, 205, 206; 128/653.1

(56) References Cited

U.S. PATENT DOCUMENTS

| 4,256,966 | * | 3/1981 | Heinz . | |
| 5,280,542 | * | 1/1994 | Ozeki et al. | 250/206.1 |
| 5,446,548 | * | 8/1995 | Gerig et al. | 378/205 |
| 5,598,269 | * | 1/1997 | Kitaevich et al. . | |

* cited by examiner

Primary Examiner—Robert H. Kim
Assistant Examiner—Pamela R. Hobden
(74) Attorney, Agent, or Firm—Gifford, Krass, Groh, Sprinkle, Anderson & Citkowski, P.C.

(57) ABSTRACT

X-ray positioning apparatus is described for aligning an x-ray imaging device (16) relative to a patient (10) to permit the operator to select and obtain an x-ray image from a selected anatomical region. A plurality of light reflective markers (14) is located on the patient's body to define certain anatomical landmarks. The apparatus comprises an x-ray source (20) and a separate light source (30) and an image sensor (33). Light reflected from the markers are detected by the image sensor (33). The image data is processed by an image processing system (46) which provides a variety of functions including determining the actual position the image device should be located to obtain the desired image. Embodiments of the invention are described.

18 Claims, 2 Drawing Sheets

MEDICAL IMAGING SYSTEMS

FIELD OF THE INVENTION

The present invention relates to medical imaging systems and in particular to a method and apparatus for aligning an imaging device relative to a patient's body. The invention is particularly, but not exclusively, applicable to the positioning of x-ray apparatus.

BACKGROUND OF THE INVENTION

When taking an x-ray of a patient, it is important to correctly position the x-ray source relative to the patient's body. Typically, the x-ray film is placed beneath a table on which the patient lies, with an ionization chamber positioned between the patient and the film. In order to ensure that the image formed on the film is in focus, the vertical distance of the x-ray source above the patient is set by the operator. Similarly, in order to ensure that the x-ray beam is incident upon the appropriate region of the patient's body, the x-ray source can also be moved by the operator in a horizontal plane.

Given the known dangers of x-ray exposure, it is important to confine the x-ray beam to that region of the body which is of particular interest. However, by utilising a smaller beam area the risk of missing the anatomical region of interest is increased. Failure to correctly capture an image of the area of interest will result in the need to take a further x-ray image, in addition to the wastage of x-ray film. Misalignment of the x-ray source in the vertical direction may also result in an out of focus image requiring that the x-ray procedure be repeated.

A known system for enabling accurate positioning of the x-ray source in the horizontal plane involves the projection of a beam of light from a light source onto a patient's body. The light source is positioned adjacent to the x-ray source and is fixed relative thereto. Typically, a x-ray radiation translucent mirror is used to direct the light beam onto the patient's body along the path taken by the x-ray beam. Prior to taking the x-ray, the operator positions the x-ray source using the light beam as a guide. Whilst in theory this system improves x-ray source alignment, in practice, regular checks must be carried out on the x-ray apparatus to ensure that the light source does not become misaligned relative to the x-ray source. Misalignment is common due to the strain placed upon the x-ray apparatus by constant movement. In addition, positioning systems of this type rely upon the expert knowledge and perception of a human operator to correctly position the light beam. X-ray images can be required for any part of the body and the operator may find difficulty in exactly centering the x-ray source to obtain a focused exposure.

SUMMARY OF THE INVENTION

It is an object of the present invention to obviate or mitigate at least one of the disadvantages of the existing system.

According to a first aspect of the present invention there is provided apparatus for aligning an imaging device relative to a human or animal body to enable an image of an operator selected anatomical region to be obtained, the apparatus comprising:

a plurality of light reflective markers for attachment to respective anatomical landmarks of the body, which landmarks mark out said anatomical region;

an image sensor arranged in use to view at least a portion of the body including attached reflective markers;

a light source arranged in use to illuminate attached reflective markers; and an image processing computer for receiving image data from the image sensor, the computer being arranged:

a) to store or access a database of standard patient records including, for each of a plurality of anatomical regions, a locating position for the imaging device relative to the positions of said anatomical landmarks;

b) to select an appropriate record from the database using operator input data for the patient to be imaged;

c) to select from the selected record a relative locating position for the imaging device using operator input data identifying the anatomical region to be imaged;

d) to determine from said image data the position of the reflective markers relative to the imaging device, and e) to determine using the selected relative locating position and the determined positions, the actual position at which the imaging device should be located in order to obtain the desired image.

The number of reflective markers required depends upon the particular area to be imaged. Typically however, a relatively small number of markers are used, e.g. between two and five.

Preferably, the image sensor comprises at least one CCD camera. Alternatively, the image sensor comprises a pair of CCD cameras which are spaced apart so as to enable a three dimensional image of a patient's body to be obtained. The resulting three dimensional image can be used in order to provide position information in three dimensions. The computer may be arranged to store focus information defining a preferred focal distance for each anatomical region. The three dimensional position information may be used to manually, or automatically set the distance of the imaging device from the patient's body. Preferably, three dimensional rendering techniques can be applied to allow a 3-D visual image of the patient to be presented to an operator, maximising the information available to the operator.

Preferably said image sensor is positioned adjacent to said light source and the light reflective markers are retro-reflective markers which tend to reflect light in the direction of the light source and the image sensor.

Preferably, the image sensor is arranged to generate image data in which areas without reflective markers are identified as black with the reflective markers being identified as light spots. This may be achieved by appropriately setting the aperture of the image sensor or by shuttering the image sensor at an appropriately high speed. Alternatively, or in addition, image data generated by the image sensor may be applied to a variable gain amplifier.

Preferably, the light source comprises a flash lamp which may be operated in synchronisation with an image sensor shutter.

Preferably, the imaging device which is aligned by the present invention is a x-ray imaging system.

Preferably, the image sensor is rigidly secured to the x-ray generating apparatus so that alignment of the image sensor relative to the x-ray tube can be accurately maintained.

In one embodiment of the invention, the image processing computer comprises a video display unit. The computer may be arranged to superimpose the determined positions of the light reflective markers on the display. The locating position of the imaging device may also be displayed.

The apparatus of the above first aspect of the present invention may comprise positioning means, coupled to said computer, for automatically positioning the imaging means The image processing computer may also be arranged to locate the imaging device at the correct focal distance, e.g. using said three-dimensional position information and using a calibration frame containing permanent markers positioned strategically on the x-ray table.

According to a second aspect of the present invention there is provided a method of aligning an imaging device relative to a human or animal body to enable an image of a selected anatomical region to be obtained, the method comprises the steps of:

attaching a plurality of light reflective markers to anatomical landmarks of the body;

illuminating the body and the reflective markers with light;

detecting light reflected from the reflective markers with an image sensor;

selecting from a database of standard patient records, a record appropriate to the patient or animal to be imaged, each record including, for each of a plurality of anatomical regions, a locating position for the imaging device relative to the positions of said anatomical landmarks;

selecting from the selected record a set of relative positions using operator input data identifying the anatomical region to be imaged;

using the selected relative position data and the determined positions of the reflective markers to determine the actual position at which the imaging device should be located in order to obtain a desired image; and positioning the imaging device at said determined position.

According to a further aspect of the invention there is provided an imaging aligning system for aligning an object to be imaged with a source of imaging radiation to which the object is exposed for creating an image of the object, said image aligning system comprising:

a first radiation source for generating an incident alignment radiation signal, a plurality of reflective markers adapted to be located at predetermined locations on the object to be imaged, reflected alignment radiation means for receiving reflected alignment radiation from the reflective markers disposed on said object, processing means coupled to the radiation source mans for providing positional information of said reflective markers relative to said object and to said source of imaging radiation, said processing means being coupled to a database of object data identifying the position for locating said source of imaging radiation relative to said object for centering said source relative to said reflective markers for exposing said object to said source of imaging information.

According to yet a further aspect of the invention there is provided apparatus for obtaining a desired image of an object, said apparatus having a source of imaging radiation to which the object is exposed and imaging means for obtaining an image of the object exposed to said radiation source, said object to be exposed having a plurality of markers defining an area of said object to be imaged, said apparatus including an aligning system stated in the above further aspect of the invention for facilitating alignment of the source of imaging radiation and said markers in order to obtain said desired image.

According to yet a further aspect of the invention there is provided a method of obtaining a desired image of an object using apparatus having a source of radiation for exposed the object to the radiating and imaging means for obtaining an image of said exposed object, said method comprising the steps of:

disposing locating reflective markers on predetermined locations of said object, transmitting a first incident signal from a signal source towards said object, collecting reflected signals from said markers, said reflected signals being indicative of the position of said markers, processing said reflected signals by comparing said marker location information with predetermined stored information from a database providing a relative position of the object to be imaged, determining the position of said reflective markers relative to said source of radiation, and aligning the source with the reflective markers in which imaging of said object produces said desired image.

For a better understanding of the present invention and in order to show how the same may be carried into effect reference will now be made, by way of example, to the accompanying drawings in which:

DETAILED DESCRIPTION OF THE PREFERRED EMBODIMENTS

Figure 1:
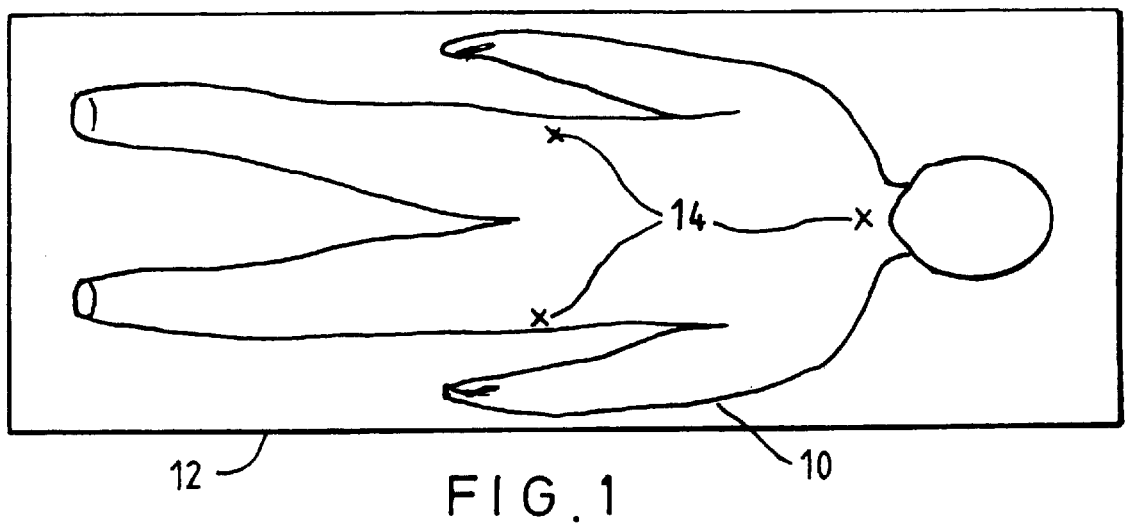
FIG. 1 is a bird's-eye view of a supine patient to be x-rayed with reflective anatomical landmarks disposed at certain positions for imaging the anterio-posterior lumbar spine.
Figure 2:
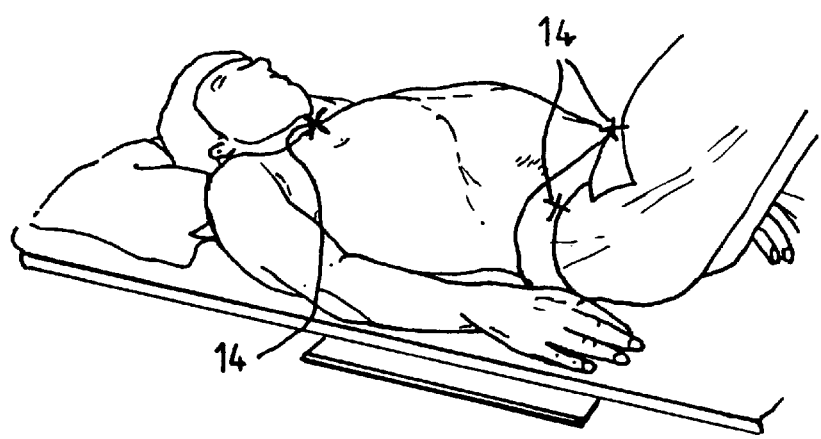
FIG. 2 is a perspective view of the patient of FIG. 1.
Figure 3:
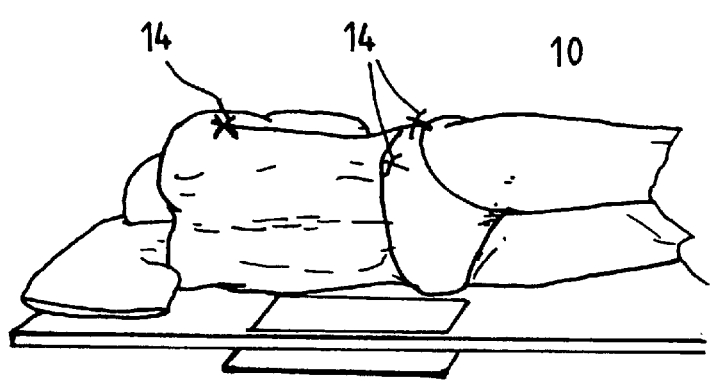
FIG. 3 is a perspective view of the patient with three reflective anatomical markers disposed for assisting in imaging a lateral view of the lumbar spine.

There is shown in FIG. 1 a bird's-eye view of a patient 10 lying on the table 12 of a x-ray system. FIG. 2 shows a perspective view of the patient. Three retro-reflective markers 14 are located on specific parts of the patient's body by an operator, usually a radiographer. The exact location of these markers depends upon the anatomical region to be imaged. In FIG. 1 where the anterio-posterior lumbar spine is to be imaged, so the markers are positioned on the sternal notch and both anterior superior iliac spine. When it is desired to obtain a lateral image of the lumbar spine, the markers are positioned, as shown in FIG. 3, on the axilla, the anterior superior iliac spine, and the posterior superior iliac spine. The required positions of the markers are readily located by an experienced radiographer.

Each of the retro-reflective markers 14 comprise a mirrored surface coated with glass micro-spheres (manufactured by 3M Corporation) which act as prisms to reflect incident light back towards its source. The markers reflect light received from a light source mainly back towards that light source and thus are highly efficient where a light detector, used to detect reflected light, is placed adjacent to the light source.

Figure 4:
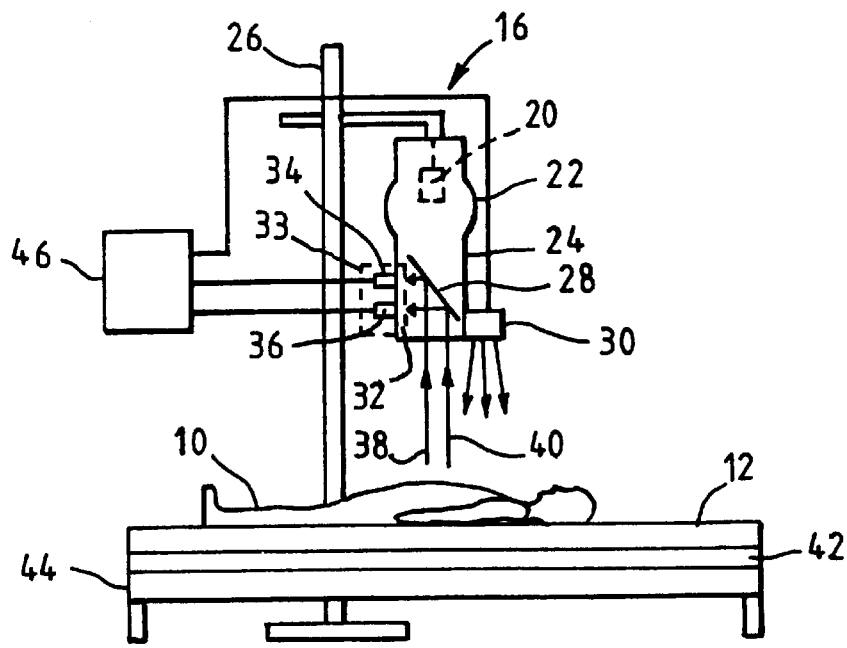
FIG. 4 illustrates a x-ray apparatus, incorporating a positioning system according to an embodiment of the present invention.

FIG. 4 illustrates a combined x-ray apparatus and positioning system, generally indicated by reference numeral 16, which is arranged to use positional information from the reflecting markers 14 to accurately align the x-ray tube apparatus, generally indicated by reference numeral 18, to the selected anatomical region of the patient's body. X-ray radiation is produced by a x-ray source 20 (shown in broken outline) contained within a lead-lined housing 22. X-rays from the source 20 are collimated within a channel 24 through which the x-ray radiation beam exits. The x-ray apparatus and positioning system 16 is adjustably mounted on a support 26 such that the height of the apparatus 16 above the patient 10 can be varied. The mounting arrangement also allows the x-ray apparatus 16 to be moved in a horizontal plane for alignment with the patient.

Contained within the x-ray apparatus channel 24 is a x-radiation translucent mirror 28, oriented at an angle of 45° to the vertical. The mirror 28 allows x-ray radiation to pass freely therethrough towards the patient and the film but presents a reflecting surface to reflected light.

Positioned inside the x-ray apparatus 16 is an infra-red strobe 30 which can generate relatively short pulses of light (i.e. 50 pulses per second at a wavelength of 980 mm). Light from strobe 30 is reflected from the patient 10 and from the reflective markers 14 is reflected towards the x-ray apparatus 14 and the strobe 30 due to the retro-reflective nature of the markers 14. Reflected light entering the channel 24 is reflected by the mirror 28 towards a side-wall 32 of the channel 24. A charge coupled camera 33 having camera elements 34,36 are mounted in this side wall for receiving the reflected radiation. Cameras elements 34,36 are spaced apart in the vertical direction such that they receive reflective light beams 38,40 from markers 14 located horizontally spaced apart positions on the patient 10.

Positioned beneath the table 12 is an ionisation chamber 42 which forms part of a known type automatic exposure device (AED). As is well known, the AED monitors the x-ray beam transmitted through the area of the patient's body under examination. Using ionisation chamber timers, the AED terminates the exposure when a sufficient quantity of radiation has been received to produce a radiographic image of the required density. The AED exercises accurate control on the quantity of radiation provided that the positioning of the patient is accurate in relation to the site of the ionisation chamber. The film is placed beneath the ionisation chamber in a mount 44 and receives the radiation which has been transmitted through the patient and AED.

Figure 5:
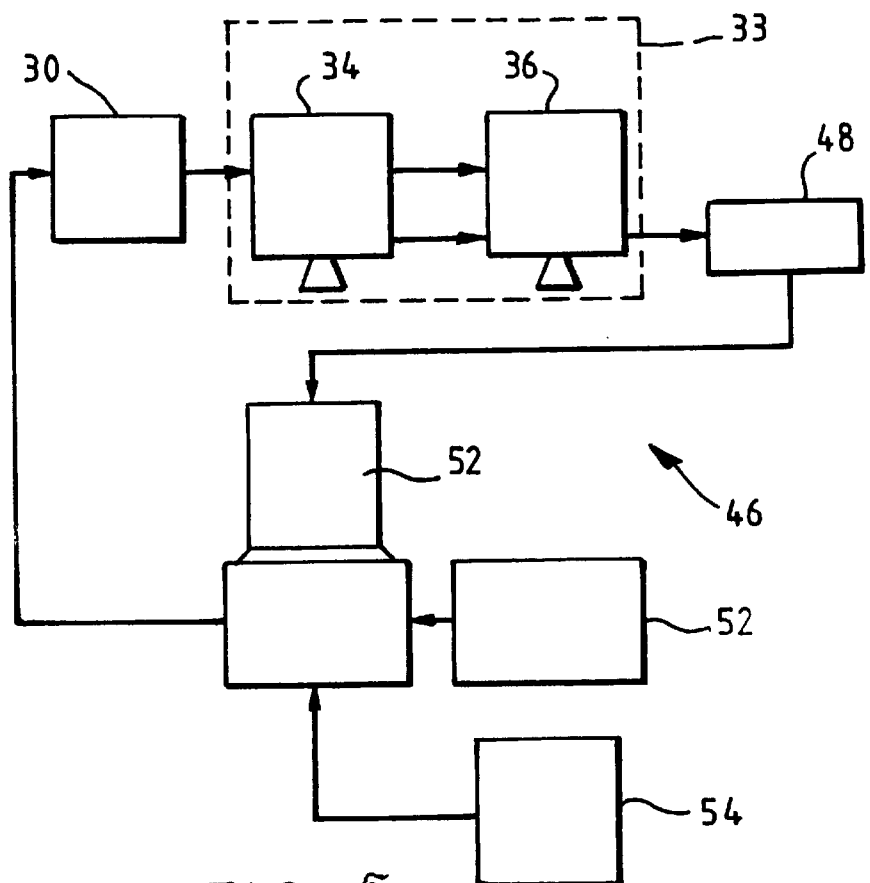
FIG. 5 is a block diagram of the system of FIG. 4.

FIG. 5 depicts the block diagram which shows schematically the image processing system, generally indicated by reference numeral 46, which is used to analyse the outputs of the two CCD camera elements 34,36 to determine alignment information for the x-ray apparatus 16. The image processing system 46 includes a video processor 48 for capturing visual information and a computer for analysing the captured information. After a predetermined time interval following activation of the strobe 30, the video processor 48 captures an image frame from each of the elements 34,36. The video processor 48 looks for transitions from dark to light in these frames and identifies any such transitions as the presence of light reflecting markers 14. The video processor scans each horizontal line of the captured image frames from left to right and identifies transitions from dark to light. Providing that transitions are located at approximately the same position on two consecutive horizontal lines, these transitions are grouped together and are identified as the site of a reflecting marker.

In order to optimise this search process, the elements 34,36 are provided with respective shutters (not shown) which open for a very short time interval during the strobe exposure. Typically, the shutters open for 1/1250 of a second. The output of each CCD element is also applied to a variable gain amplifier (not shown) within the video processor 48 the gain of which is adjusted so that the intensity produced by the reflective markers 14 is set as a 'normal' intensity. This set-up generates image data where the reflective markers 14 show up as bright spots while remaining areas are black. The system may be further optimised by minimising the background light levels in the room containing the x-ray apparatus.

The resulting position data, which defines the absolute position of the retro-reflective markers 14 relative to the patient 10 and the x-ray apparatus 16, is delivered from the video processor to the computer 50. The computer 508 contains a database of standard patient records. The patients selected for the database cover a range of heights and weights, and each record contains anatomical position data for each of a number of anatomical regions. This anatomical data defines the position at which the x-ray apparatus 16 should be positioned for the X-ray to be centred upon the required anatomical region, relative to the positions of the reflecting markers 14 on the anatomical landmarks.

The radiographer uses a keyboard 52 to enter the height, weight and identification of the patient 10 to be imaged. The computer 50 then selects the appropriate record from the stored database. The radiographer then also selects the anatomical region of interest and the appropriate data is extracted from the selected record. From a knowledge of the actual positions of the reflective markers 14, and the locating position of the x-ray apparatus 16 relative to these markers, the computer is able to calculate the actual locating position. This positional information can either be displayed to the operator who can then manually position the x-ray apparatus or the positional information can be fed to automatic x-ray apparatus adjustment means for automatically repositioning the apparatus 16.

The system 46 optionally contains a display monitor 54 for displaying image data generated by one of the CCD cameras 34,36. The cameras 34,36 may be arranged to generate normal continuous image data for display on the monitor 54, the cameras only being shuttered for a relatively short time period to obtain reflective marker position information. Once this position information has been obtained, it can be overlaid on the image of the patient's body on the display. This allows the operator to visually confirm the correct identification of the reflective markers 14 before automatic alignment of the x-ray apparatus occurs. Similarly, the computer may be arranged to overlay the determined locating position of the x-ray apparatus on the display.

As another example, to obtain an anterio-posterior view of the knee joint a first marker would be placed 2.5 cm above the superior aspect of the patella, a second marker 2.5 cm below the tibial tuberosity, and third and fourth markers on the lateral and medial borders adjacent to the apex of the patella. To obtain a lateral view of the knee joint, a first marker would be placed 2.5 cm above the upper border of the knee on the medial side, and a second marker placed 2.5 cm below the apex of the patella on the medial side.

In addition to anatomical positioning, patient movement can be monitored visually, thus allowing the operator to correct patient position relative to any movement. This function therefore provides an assessment of the correctness of positioning before the x-ray exposure has been made. Monitoring of patient movement continues until the exposure has been completed.

Various modifications may be made to the embodiments hereinbefore described without departing from the scope of the invention. The x-ray system and positioning apparatus can be used to image an animal body and the light source used could be replaced by an infra-red source with an infra-red camera. The positioning system may be used with any other suitable medical imaging system where alignment of the source of radiation with the part of the patient to be imaged is required.

What is claimed is:

1. Apparatus for aligning an imaging device relative to a human or animal body to enable an image of an operator selected anatomical region to be obtained, the apparatus comprising:

a plurality of light reflective markers for attachment to respective anatomical landmarks of the body, which landmarks mark out said anatomical region;

an image sensor arranged in use to view at least a portion of the body including said reflective markers attached thereto;

a light source arranged in use to illuminate said reflective markers attached to said body; and an image processing computer for receiving image data from the image sensor, the computer being operative:

a) to communicate with a database of standard patient records including, for each of a plurality of anatomical regions, a locating position for the imaging device corresponding to each of said anatomical landmarks;

b) to select an appropriate record from the database using operator input data for a patient to be imaged;

c) to select from the selected record a particular locating position for the imaging device using operator input data identifying the anatomical region to be imaged;

d) to determine from said image data a position corresponding to each of the reflective markers relative to the imaging device; and e) to determine using the selected locating position and the determined position, actual position at which the imaging device should be located in order to obtain the desired image.

2. Apparatus as claimed in claim 1 wherein the image sensor comprises at least one CCD camera.

3. Apparatus as claimed in claim 2 wherein the image sensor comprises a pair of CCD cameras which are spaced apart so as to enable a three dimensional image of a patient's body to be obtained.

4. Apparatus as claimed in claim 1 wherein said image sensor is positioned adjacent to said light source and the light reflective markers are retro-reflective markets which tend to reflect light in the direction of the light source and the image sensor.

5. Apparatus as claimed in claim 1 wherein the image sensor is operative to generate image data in which areas without reflective markers are identified as black, with the reflective markers being identified as light spots.

6. Apparatus as claimed in claim 5 wherein said image data is generated by appropriately setting an aperture of the image sensor or by shuttering the image sensor at an appropriately high speed.

7. Apparatus as claimed in claim 6 wherein said image data generated by the image sensor is applied to a variable gain amplifier.

8. Apparatus as claimed in claim 1 wherein the light source comprises a flash lamp and said image sensor includes a shutter, said flash lamp being operated in synchronisation with said image sensor shutter.

9. Apparatus as claimed in claim 1 wherein the imaging device is aligned by an x-ray imaging system and the image sensor is rigidly secured to an x-ray tube so that alignment of the image sensor relative to the x-ray tube is accurately maintained.

10. Apparatus as claimed in claim 1 wherein the image processing computer includes a video display unit and the computer is operative to superimpose the determined positions of the light reflective markers on the display.

11. Apparatus as claimed in claim 1 wherein said apparatus includes positioning means coupled to said computer for automatically positioning the imaging device.

12. Apparatus as claimed in claim 3 wherein the image processing computer is operative to locate the imaging device at a correct focal distance, using three-dimensional position information and using a calibration frame containing permanent markers positioned strategically on an x-ray table.

13. A method of aligning an imaging device relative to a human or animal body to enable an image of a selected anatomical region to be obtained, the method comprises the steps of:

attaching a plurality of light reflective markers to anatomical landmarks of the body;

illuminating the body and the reflective markers with light;

detecting light reflected from the reflective markers with an image sensor to generate image data;

selecting from a database of standard patient records, a record appropriate to the patient or animal to be imaged, each record including, for each of a plurality of anatomical regions, a locating position for the imaging device corresponding to each of said anatomical landmarks;

selecting from the selected record a set of position data using operator input data identifying the anatomical region to be imaged;

determining from said image data a position corresponding to each of the reflective markers relative to the imaging device;

using the selected position data and the determined positions of the reflective markers to determine the actual position at which the imaging device should be located in order to obtain a desired image; and positioning the imaging device at said determined position.

14. An imaging aligning system for aligning a portion of a human or animal body to be imaged with an x-ray source of imaging radiation to which the object is exposed for creating, an image of the body portion said image aligning system comprising:

a first x-ray radiation source for generating an incident alignment radiation signal, a plurality of reflective markers adapted to be located at predetermined locations on the body portion to be imaged, reflected alignment radiation means for receiving reflected alignment radiation from the reflective markers disposed on said body portion, processing means coupled to the x-ray radiation source for providing positional information of said reflective markers relative to said body portions and to said x-ray source of imaging radiation, said processing means being coupled to a database of object data identifying a position for locating said x-ray source of imaging radiation relative to said portion for centering said source relative to said reflective markers for exposing said body portion to said x-ray source of imaging radiation.

15. An imaging aligning system as claimed in claim 14 wherein said processing means is coupled to display means for displaying positional information of the x-ray source of said imaging radiation.

16. An imaging system as claimed in claim 15 wherein the positional information is coupled to image radiation source adjustment means for adjusting automatically the position of said x-ray image radiation source relative to said reflective markers.

17. The system of claim 14 further including a second x-ray, source of imaging radiation to which the body portion is exposed and imaging means for obtaining an image of the body portion exposed to said second x-ray source of imaging radiation, said second x-ray source of imaging radiation being aligned by said image aligning system in order to obtain said image.

18. A method of obtaining a desired image of a portion of a human or animal body using apparatus having an x-ray source of radiation for exposing the body portion to the radiating and imaging means for obtaining said image of said exposed body portion, said method comprising the steps of:

disposing locating reflective markers on predetermined locations on said body portion, transmitting a first incident signal from a signal source towards said body portion, collecting reflected signals from said markers, said reflected signals being indicative of the position of said markers, processing said reflected signals by comparing said marker location information with predetermined stored information from a database providing a relative position of the body portion to be imaged, determining the position of said reflective markers relative to said x-ray source of radiation, and aligning the source with the reflective markers such that imaging of said body portion produces said desired image.

* * * * *